United States Patent [19]

Powell

[11] Patent Number: 4,536,897
[45] Date of Patent: Aug. 27, 1985

[54] INTRAOCULAR LENS

[76] Inventor: Robert M. Powell, 686 Crestwood Dr., Gaylord, Mich. 49735

[21] Appl. No.: 511,849

[22] Filed: Jul. 8, 1983

[51] Int. Cl.³ .......................... A61F 1/16; A61F 1/24
[52] U.S. Cl. .................................... 623/6; 128/303 R
[58] Field of Search .......................... 3/13; 128/303 R

[56] References Cited

U.S. PATENT DOCUMENTS

| 4,268,921 | 5/1981 | Kelman | 3/13 |
| 4,365,360 | 12/1982 | Ong | 3/13 |
| 4,418,431 | 12/1983 | Feaster | 3/13 |

OTHER PUBLICATIONS

"Ovoid Optic Posterior Chamber Intraocular Lens: The First One Hundred Cases", by Henry M. Clayman, AM Intra-Ocular Implant Soc. J., vol. 8, Fall 1982, pp. 343–345.
The Simcoe Posterior Chamber Lens (Brochure by Cilco) Cilco, Inc., 1616 13th Ave., Huntington, West Va. 25701, 5 pages, Feb. 1980.
New Posterior Chamber Intraocular Lens (Lester Posterior Chamber Lens) Advertisement–Intermedics Intraocular Inc., P.O. Box 70670, Pasadena, CA 91107, 2 pages, Aug. 1982.
Lens Styles from Cilco, Advertisement Brochure Cilco, Cilco, Inc., 1616 13th Ave., Box 1680, Huntington, West Va. 25717, 6 pages, Oct. 1982, p. 4 and Simcoe II Posterior Chamber Lens.

Primary Examiner—Ronald L. Frinks
Attorney, Agent, or Firm—Krass and Young

[57] ABSTRACT

A new type of intraocular lens is provided for implantation in the eye following cataract extraction. The new lens is uniquely structured at the edge of the lens optic to provide advantages both in implanting and repositioning the lens and in avoiding blocking of lens perforations.

14 Claims, 7 Drawing Figures

U.S. Patent    Aug. 27, 1985    4,536,897
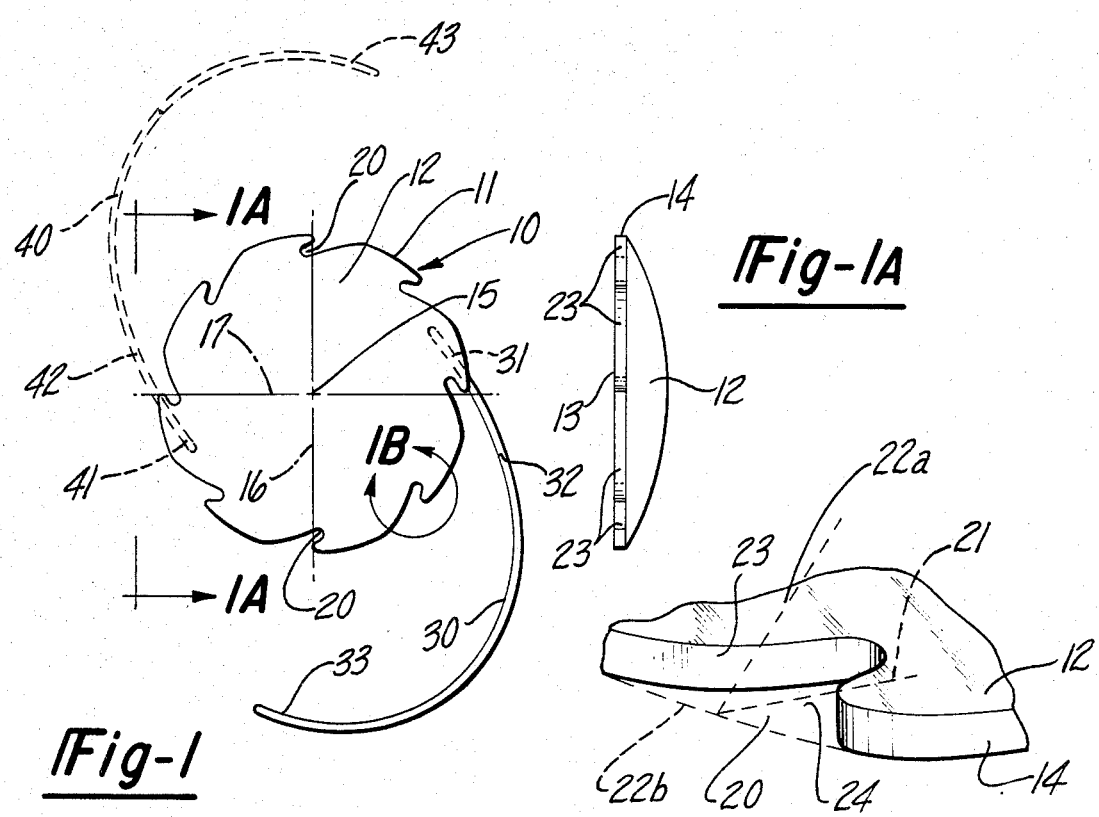
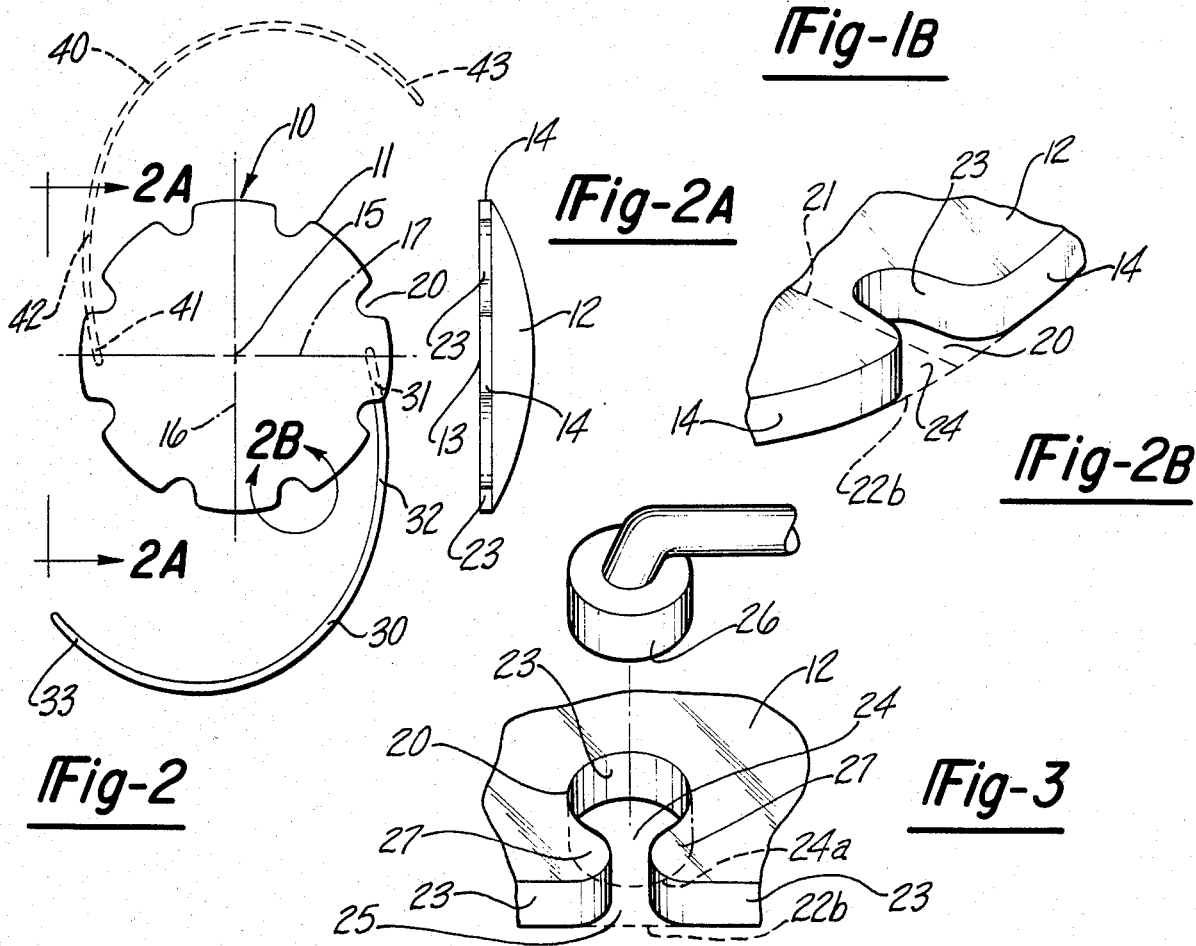

INTRAOCULAR LENS

DESCRIPTION

1. Technical Field

This invention relates to artificial body members and, more particularly, to a unique kind of intraocular lens (IOL) useful for implantation in the chamber of the eye after capsular extraction.

2. Background Art

In the human eye, the lens is situated behind the pupil and iris, and functions to focus light entrant through the cornea and pupil onto the retina at the rear of the eye. The lens is a biconvex, highly transparent structure made of slender, curved rod-shaped ectodermal cells in concentric lamellae surrounded by a thin lens capsule. The lens capsule is supported at its periphery by suspensory ligaments, called zonules, that are continuous with the ciliary muscle. Contraction of this muscle relaxes the zonules, allowing the lens to become more spherical, thereby altering its focal length.

A cataract condition results when the material within the lens capsule become clouded, thereby obstructing the passage of light. To correct this condition, two forms of surgery are used. One is intracapsular extraction, and the other is extracapsular extraction. In intracapsular cataract extraction, the surgeon severs the zonules or suspensory ligaments about the entire periphery of the capsule, and removes the entire lens with the capsule and its content material intact. In extracapsular cataract extraction, an incision is made through the front wall (the "anterior capsule") of the lens, and the clouded cellular material within the capsule is removed through this opening. Various scraping, suction or phacoemulsification techniques are used to accomplish such extraction. The transparent rear capsule wall (the "posterior capsule") remains in place in the eye. Also remaining in place are the zonules, and peripheral portions of the anterior capsule (the "anterior capsule flaps").

Both intracapsular and extracapsular extraction eliminate the light blockage due to the cataract. However, the light now entrant through the cornea and pupil is totally unfocused since the eye is aphakic, that is, the eye no longer has a lens. Appropriate focusing can be achieved by a lens (i.e., a contact lens) exterior to the eye. This approach, though generally satisfactory, has the disadvantage that when the external lens is removed (i.e., when the contact lens is "taken out"), the patient effectively has no sight. A preferred alternative is to implant an artificial lens directly within the aphakic eye.

Various forms of intraocular lenses are known. Generally these fall into two major classes, the anterior chamber lenses which are situated forward of, or mounted to the iris, and posterior chamber lenses which are situated behind the iris and may be mounted either within the ciliary sulcus or groove or within the cleft or fornix of the capsule which remains in place after extracapsular surgery.

The mounting or fixation of intraocular lenses is done by various means such as clips, closed or open loops, filaments, or other haptic supports attached to the lens body and anchored within the chamber, as described. Suturing may also be used for attachment purposes. Some forms of lens are perforated, that is, they include one or more locating holes in the lens optic for the purpose of manipulating the lens during surgery. In this case, the margins of the locating hole are used as a support to receive the distal end of a hand-held tool, such as a Sinskey hook, and to be guided and/or rotated (dialed) thereby into the desired position of insertion within the eye chamber. The locating hole is also used post-operatively for corrective or secondary intraocular surgery such as may be required to reposition the lens. Often, the difficulty in such a procedure is that the hole may be blocked by intraocular material or ingrowth from the posterior capsule, or otherwise not visible or accessible to the surgeon.

It is therefore an object of the present invention to provide an improved intraocular lens that overcomes the disadvantages of prior art lenses.

It is another object of the invention to provide an intraocular lens which is specially structured with means facilitating implantation and positioning.

It is still another object of the invention to provide a new lens of the type described which is structured for facile manipulation and when implanted tends to resist ingrowth of tissue.

DISCLOSURE OF THE INVENTION

These and other objects are achieved by providing, for implantation or positioning in the chamber of an eye after capsular extraction, an intraocular lens having a unique structural configuration at the edges of the lens, presently to be described, enabling surgical manipulation of the lens for implantation and positioning.

The intraocular lens of the invention, in one embodiment, comprises an imperforate lens optic having an anterior face and a posterior face, the circumference of each face having a continuous curving common edge configured with at least one axial socket recess open to said edge and faces, and at least two opposed flexibly compressible haptic loops adapted for rotating the lens and centering the lens optic on the optical axis, the socket recess having bearing surfaces adapted to receive the distal end of a surgical tool and to be moved by the tool for positioning the lens in a surgical procedure. In one preferred embodiment, the lens optic comprises four quadrants having a socket recess in at least one of the four quadrants, preferably comprising at least one socket recess, and more preferable two, in each of the quadrants. Suitably, the perimetral location of two or more recesses is balanced so that there is equal circumferential spacing among the recesses. The shape of the anterior and posterior faces of the lens optic may be varied and in one embodiment preferably is circular. In other preferred embodiment, the lens faces are oval or ovoid. The haptic loops may take any of a variety of forms suitable for fixating and centering the lens on the central optical axis of the eye. Thus, the haptic loops may be in the plane of the lens optic or forwardly or rearwardly angulated, and may be open or closed loops, edge-mounted or face-mounted with respect to the lens optic, C-loops, J-loops, or other similar haptic loops. In one preferred embodiment, the loops are paired C-loops, preferably broadly curved circular C-loops. In a preferred embodiment for purposes of rotational positioning, the loops are edge-mounted at a slant from the direction of intended rotation.

BRIEF DESCRIPTION OF THE DRAWINGS

The invention will be more fully understood by reference to the following detailed description and accompanying drawing in which:

FIGS. 1 and 2 are plan views of preferred embodiments of an intraocular lens according to the invention;

FIGS. 1a and 2a are side views in elevation taken on lines 1a—1a and 2a—2a of FIGS. 1 and 2 of the intraocular lens;

FIGS. 1b and 2b are perspective views of a recess in respective segments of the edge of the lens optic of FIGS. 1 and 2; and FIG. 3 is a similar view of an undercut recess of an edge segment and an insertion tool segment showing the dimensional relationship of the recess to the distal end of the insertion tool.

DESCRIPTION OF FURTHER PREFERRED EMBODIMENTS AND BEST MODE OF PRACTISING THE INVENTION

The following description concerns further preferred embodiments of the invention, for the purpose of illustrating the invention. Thus, this description is not to be taken in a limiting sense.

Referring to the drawing, FIG. 1 shows a preferred embodiment in which the intraocular lens 10 has a generally circular lens optic 11. The optic optionally can be oval in shape or ovoid which shape has certain advantages such as a narrow geometry for purposes of insertion through an incision. The optic 11 has an anterior face 12 and a posterior face 13 at the circumference of which is a continuous curving edge 14, common to both faces 12 and 13, configured with axial notches or socket recesses 20 that are open to the faces 12 and 13 and to the edge 14 (shown in broken outline). The center 15 of the lens is defined by the intersection of diameters 16 and 17. The notches or recesses 20, according to the invention, have several advantages for both the surgeon and the patient. The recesses are configured with smooth edges so as not to hang up or catch, that is, the recesses do not interfere in this respect with the insertion of the lens. Also, unlike prior art perforated lenses, they have an open profile that tends, after implantation, not to become readily blocked by intraocular material or by ingrowth of tissue.

For purposes of centration and fixation, the lens 10 includes superior and inferior haptic supports or loops 30 and 40 that are mounted in the plane of the lens optic 11 by edge-staking (not shown) at the base 31 and 32 of the loops (shown in broken outline). The loops have leading edges 32 and 42 and trailing edges 33 and 43. As seen in FIG. 1a, the anterior face 12 of the lens optic 11 is convex, and the lens edge 14 occupies a major proportion of the circumference of the optic. As seen in FIG. 1b, the recess 20 has a central axis 21 (shown in broken outline) that is slanted at an angle (preferably about 60 to 85 degrees) from the lens radius 22a (shown in broken outline). The angle of slant is such that when a tool piece engages the walls 23 and is forced into the recess for positioning or dialing the lens, the axial force transmitted to the leading and trailing edges advantageously has a tangential vector that serves to compress the haptics and thereby cause them to insert more readily and freely within the eye chamber. The recess 20 of FIG. 1b constitutes a chamber defined or circumscribed by the recess wall 23, the lens circumference segment 22b of the lens optic, and the respective planes of the anterior face 12 and the posterior face 13, the latter plane or plane segment being designated as chamber base 24.

FIG. 2 illustrates a preferred embodiment of an intraocular lens in which the notches or recesses 20 of the optic are each rounded or semi-cylindrical and symmetrical about their respective axis 21, the latter axis coinciding with the radius 22a of the optic.

FIG. 3 illustrates a preferred embodiment of an intraocular lens in which each lens notch or recess 20 is undercut (with shoulders 27), constituting a main chamber having a circular base 24 outlined in part by a perimeter segment 24a (shown in broken outline) and a side chamber of constricted dimension having a base 25 defined by the main chamber segment 24a and a segment 22b of the circumference. The constriction, for example, can be about 0.2 mm. so that, where the main chamber is about 0.4 mm. in dimension, the constriction in the side chamber (the distance between the shoulders 27) is about 0.2 mm. Also shown in FIG. 3 is the distal end 26 of a surgical tool illustrating how the geometry of the distal end 26 matches that of the main chamber of recess 20 and how, in a surgical procedure, the tool can be presented for insertion of the distal end in a matching fit into main chamber of the recess. When so inserted, the distal end 26 is advantageously captured and prevented from edgewise withdrawal. This enables the tool to guide and control the insertion of the lens in any direction in the plane of the lens optic.

As indicated, the lens optic 12 can, according to the invention, be provided with one or more recesses 20. For example, if one regards the ends of diameters 16 and 17 as representing 3, 6, 9 and 12 o'clock positions, a single notch or recess can advantageously be located at or near a 12 o'clock position of the edge. Thus, when the lens is inserted through a surgical incision, the same can be accomplished by inserting the inferior loop 43 and partially inserting the lens optic 12 to a point where the lens recess at 12 o'clock is left exposed to open view. The optic can then be dialed or rotated into the surgical site in counter-clockwise fashion, by engaging the recess with the distal end of a tool such as iris hook or Sinskey hook and pushing or manipulating the lens with torquing and sliding force into a position of centration. Similarly, the optic 12 can advantageously be provided with a recess 20 in each of the quadrants defined by the lens diameters 16 and 17. A preferred lens is one having recesses 20 in all quadrants so that, for purposes of repositioning such as required by corrective surgery, a wider choice of tool-bearing sites is available to restore centration.

The dimensions of the notches or socket recesses 20 can be varied, preferably being of a size accommodating the distal end of an insertion tool. For example, for an optic size of 6 mm. the recess may be approximately 0.4 mm. in diameter or width dimension or larger. The surfaces of the recess are smooth and otherwise suitable for surgical purposes. The lens optic and the haptic supports can be made of conventional materials by available methods of manufacture. For example, the lens optic is preferably made of an optical quality of polymethylmethacrylate, such as Perspex CQ polymethylmethacrylate. The lens haptic is preferably made of polypropylene such as Prolene polypropylene. The recesses can be made in any suitable way such as by molding or cutting, lathing, punching or jigging from a single block, followed by appropriate finishing or polishing. Advantageously, fabrication of recesses, as opposed to the drilling of locator holes of conventional lens bodies, offers economies of manufacture and freedom from chipping and fracturing.

What is desired to claim as my exclusive property in the invention, as described, is the following.

What is claimed is:

1. An intraocular lens useful for implantation or positioning in the chamber of an eye after capsular extraction, comprising:

an imperforate lens optic having an anterior face and a posterior face, the circumference of each face having a continuous curving common edge configured with at least one continuous curving axial socket recess open to said edge and faces, and haptic support means adapted for rotating the lens and centering the lens optic on the optical axis, the socket recess having bearing surfaces of a size adapted to receive and accommodate in close-fitting relation by open edge-access the distal end of a surgical tool to thereby enable the lens to be rotated or dialed and thus moved by the tool in the plane of the lens for positioning of the lens in a surgical procedure.

2. An intraocular lens according to claim 1 wherein the lens optic comprises four quadrants having a socket recess in at least one of the quadrants.

3. An intraocular lens according to claim 2 wherein each quadrant is provided with at least one socket recess.

4. An intraocular lens according to claim 3 wherein each quadrant comprises two socket recesses.

5. An intraocular lens according to claim 1 wherein the faces of the lens optic are circular.

6. An intraocular lens according to claim 1 wherein the haptic support means comprise paired broadly curved circular C-loops.

7. An intraocular lens according to claim 6 wherein the loops are edge-mounted at a slant for rotation of the lens.

8. An intraocular lens according to claim 1 wherein the bearing surfaces of the socket recess define a substantially semi-cylindrical chamber.

9. An intraocular lens according to claim 7 wherein the bearing surfaces of the socket recess define a chamber slanted at an angle accommodating rotation of the lens.

10. An intraocular lens useful for implantation or positioning in the chamber of an eye after capsular extraction, comprising:

a lens optic having an anterior face and a posterior face, the circumference of each face having a continuous curving common edge configured with at least one axial socket recess open to said edge and faces, and haptic support means adapted for rotating the lens and centering the lens optic on the optical axis, the socket recess having bearing surfaces adapted to receive the distal end of a surgical tool and to be moved by the tool for positioning of the lens in a surgical procedure and being undercut from the edge and configured to receive the end of a surgical tool in close fitting relation to accommodate implantation or repositioning in a surgical procedure.

11. An intraocular lens according to claim 10 wherein each socket recess comprises a main chamber and a side chamber, the main chamber having bearing surfaces dimensioned in width to receive the distal end of a surgical tool in a predetermined matching fit and the side chamber being open to the edge of the lens optic and in open communication with the main chamber.

12. An intraocular lens according to claim 11 wherein the width of the side chamber is less than that of the main chamber thereby preventing edgewise withdrawal of the distal end of the surgical tool from the socket recess.

13. An intraocular lens according to claim 12 wherein the main chamber is approximately 0.4 mm in diameter.

14. An intraocular lens according to claim 13 wherein the side chamber is approximately 0.2 mm. in dimension.

* * * * *

REEXAMINATION CERTIFICATE (2735th)
United States Patent [19]
Powell

[11] B1 4,536,897
[45] Certificate Issued Nov. 21, 1995

[54] INTRAOCULAR LENS

[76] Inventor: Robert M. Powell, 686 Crestwood Dr., Gaylord, Mich. 49735

Reexamination Request:
No. 90/003,393, Apr. 12, 1994

Reexamination Certificate for:
Patent No.: 4,536,897
Issued: Aug. 27, 1985
Appl. No.: 511,849
Filed: Jul. 8, 1983

[51] Int. Cl.$^6$ ..................... A61F 2/16
[52] U.S. Cl. ..................... 623/6
[58] Field of Search ..................... 623/6

[56] References Cited

U.S. PATENT DOCUMENTS

| | | |
|---|---|---|
| 4,025,965 | 5/1977 | Siegmund . |
| 4,092,743 | 6/1978 | Kelman . |
| 4,122,556 | 10/1978 | Poler . |
| 4,174,543 | 11/1979 | Kelman . |
| 4,253,200 | 3/1981 | Kelman . |
| 4,296,501 | 10/1981 | Kelman . |
| 4,298,994 | 4/1981 | Clayman . |
| 4,370,760 | 7/1983 | Kelman . |
| 4,418,431 | 12/1983 | Feaster . |
| 4,485,499 | 12/1984 | Castleman . |
| 4,504,981 | 3/1985 | Walman . |

OTHER PUBLICATIONS

"The Simcoe Posterior Chamber Lens", Feb. 1980, 5 page Advertising Brochure; CILCO.
Robert L. Stamper; "Intraocular Lens Data"; Aug. 1992; Ophthalmology, vol. 89 No. 8S, pp. 125–179.
Richard H. Keates, et al.; "The Kelman and Other Anterior Chamber Lenses"; Ophthalmic Surgery, vol. 11, No. 10, Oct. 1980.
The Jouranl of The American Academy of Ophthalmology; Nov. 1980; vol. 87 No. 11; Advertisement for Medical Workshop.
Richard P. Kratz, et al.; "The Shearing Intraocular Lens: a Report of 1,000 Cases"; Jan. 1981; Am Intra–Ocular Soc. J. vol. 7.
"New Posterior Chamber Intraocular Lens"; Advertisement to Intermedics Intraocular Inc.; Aug. 1982.
C. William Simcoe, M.D.; "Simcoe Posterior Chamber Lens: Theory, Techniques and Results"; Apr. 1981; Am Intra–Ocular Implant Soc.
"A Practical Posterior Chamber Lens"; Jul./Sep. 1978; Contact Lens, vol. 4 No. 3.
Kelman Posterior Chamber Model PC–30; Advertisement for Heyer–Schulte Medical Optics Center; Jul. 1979.
Kelman Omnifit II Anterior Chamber IOL; Advertisement to Precision Cosmet Co., Inc.; Jan. 1983.
Kelman Anterior Chamber Model AC–20; Advertisement to American Medical Optics; Aug.
"Lens Styles from CILCO"; Oct. 1982; Advertisement.
C. William Simcoe; "An Ounce of Prevention"; American IOL Implant Society Journal; Jan. 1978; vol. 4, No. 1; pp. 39–44.

*Primary Examiner*—Mary Beth Jones

[57] ABSTRACT

A new type of intraocular lens is provided for implantation in the eye following cataract extraction. The new lens is uniquely structured at the edge of the lens optic to provide advantages both in implanting and repositioning the lens and in avoiding blocking of lens perforations.

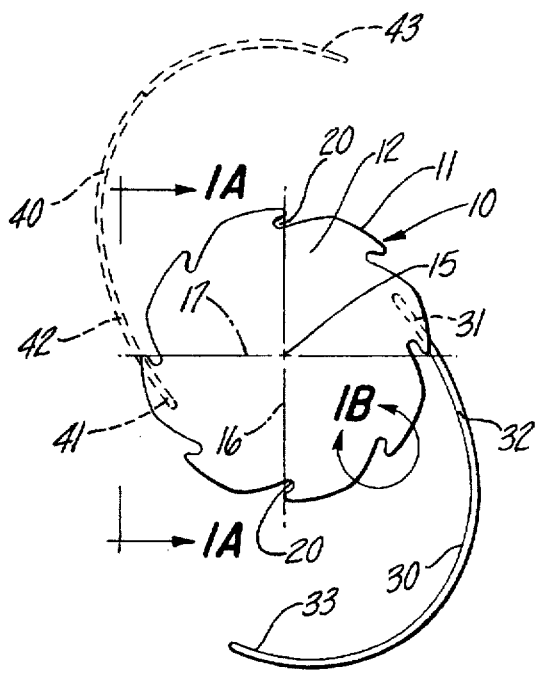

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 4, 7, 9, 10–14 is confirmed.

Claims 1–3, 5, 6 and 8 are cancelled.

New claims 15, 16 and 17 are added and determined to be patentable.

15. *An intraocular lens useful for implantation or positioning in the chamber of an eye after cataract removal, comprising:*

*an imperforate lens optic having an anterior face and a posterior face, the circumference of each face having a continuously curving common edge configured with at least one continuously curving axial socket recess open to said edge and faces, and haptic support means adapted for rotating the lens and centering the lens optic on the optical axis, the socket recess having bearing surfaces of a size adapted to receive and accommodate in close-fitting relation by open edge-access the distal end of a surgical tool to thereby enable the lens to be rotated or dialed and thus moved by the tool in the plane of the lens for positioning of the lens in a surgical procedure, said bearing surfaces of said socket recess defining a chamber slanted at an angle accommodating rotation of the lens.*

16. *An intraocular lens useful for implantation or positioning in the chamber of an eye after cataract removal, comprising:*

*an imperforate lens optic having an anterior face and a posterior face, the circumference of each face having a continuously curving common edge configured with at least one continuously curving axial socket recess open to said edge and faces, and haptic support means adapted for rotating the lens and centering the lens optic on the optical axis, the socket recess having bearing surfaces of a size adapted to receive and accommodate in close-fitting relation by open edge-access the distal end of a surgical tool to thereby enable the lens to be rotated or dialed and thus moved by the tool in the plane of the lens for positioning of the lens in a surgical procedure, wherein said socket recess is undercut in a single direction from said open edge access.*

17. *An intraocular lens as recited in either claims 15 or 16 wherein said lens is made from a single block of material followed by appropriate finishing or polishing.*

* * * * *